United States Patent
Karim et al.

(12) 
(10) Patent No.: US 6,337,424 B1
(45) Date of Patent: Jan. 8, 2002

(54) CATALYSTS OXIDATION OF LOWER OLEFINS TO UNSATURATED ALDEHYDES, METHODS OF MAKING AND USING THE SAME

(75) Inventors: Khalid Karim, Manchester (GB); Yajnavalkya Subrai Bhat, Riyadh (SA); Syed Irshad Zaheer, Riyadh (SA); Asad Ahmad Khan, Riyadh (SA)

(73) Assignee: Saudi Basic Industries Corporation (SA)

( * ) Notice: Subject to any disclaimer, the term of this patent is extended or adjusted under 35 U.S.C. 154(b) by 0 days.

(21) Appl. No.: 09/560,989

(22) Filed: Apr. 28, 2000

(51) Int. Cl.$^7$ .............................................. C07C 45/00
(52) U.S. Cl. ...................... 568/478; 568/470; 568/476; 568/479; 568/480
(58) Field of Search ................................. 568/470, 476, 568/478, 479, 480

(56) References Cited

U.S. PATENT DOCUMENTS

| | | |
|---|---|---|
| 4,224,193 A | 9/1980 | Vanderspurt |
| 4,267,385 A | 5/1981 | Umenura |
| 4,267,386 A | 5/1981 | Vanderspurt |
| 4,432,817 A | 2/1984 | Frankel |
| 4,438,217 A | 3/1984 | Takata |
| 4,442,308 A | 4/1984 | Arntz |
| 4,916,103 A | 4/1990 | Martan |
| 5,072,052 A | 12/1991 | Boeck |
| 5,144,090 A | 9/1992 | Honda |
| 5,300,707 A | 4/1994 | Caillod |
| 5,532,199 A | 7/1996 | Watanbe |
| 6,080,893 A | 6/2000 | Hecquet |

FOREIGN PATENT DOCUMENTS

| | | |
|---|---|---|
| DE | 3300044 | 1/1987 |
| EP | 417723 | 3/1991 |
| EP | 460932 | 12/1991 |
| EP | 861819 | 9/1998 |
| JP | 56055331 | 5/1981 |
| JP | 3170445 | 7/1991 |
| JP | 3294239 | 12/1991 |
| JP | 4295438 | 10/1992 |
| JP | 6031171 | 2/1994 |
| JP | 8003093 | 1/1996 |
| JP | 8040969 | 2/1996 |
| JP | 11343261 | 12/1999 |

*Primary Examiner*—Sreeni Padmanabhan
*Assistant Examiner*—J. Parsa
(74) *Attorney, Agent, or Firm*—Kramer Levin Naftalis & Frankel LLP

(57) ABSTRACT

The present invention provides a catalyst composition for the production of unsaturated aldehydes by the oxidation of the corresponding olefins, and methods of making and using such catalyst compositions. The catalysts of the present invention include compositions of the formula:

$$Mo_aPd_bBi_cFe_dX^1_eX^2_fX^3_gO_z,$$

wherein $X^1$ is an element selected from Co, Ni, V, Pt, Rh, or mixtures thereof; $X^2$ is an element selected from Al, Ga, Ge, Mn, Nb, Zn, Ag, P, Si, W, or mixtures thereof; $X^3$ is an element selected from K, Mg, Rb, Ca, Sr, Ba, Na, In, or mixtures thereof; a is 1; b is $0<b<0.3$; c is $0<c<0.9$; d is $0<d<0.9$; e is $0<e<0.9$; f is $0<f<0.9$; g is $0<g<0.3$; and z is an integer representing the number of oxygen atoms required to satisfy the valency of Mo, Pd, Bi, Fe, $X^1$, $X^2$, and $X^3$ in the catalyst composition. Using the methods of the present invention, one may effectively oxidize the desired starting materials at relatively high levels of conversion, selectivity, and productivity, and with minimal side products.

15 Claims, No Drawings

CATALYSTS OXIDATION OF LOWER OLEFINS TO UNSATURATED ALDEHYDES, METHODS OF MAKING AND USING THE SAME

The redox characteristic of a mixed metal oxide catalyst is a key factor in controlling the activity and oxygenation function of the catalyst. These characteristics depend on the type of metal oxide mixed and their concentration. See, "Oxidative Dehydrogenation of Lower Alkane on Vanadium Based Catalysts", by E. Mamedov and V. Corberan, *Applied Catalysis*, vol. 217, pages 1–40 (1995). It would be desirable to derive a catalyst composition containing a specific combination of metal elements with suitable properties or characteristics to generate a redox characteristic catalyst having a significant impact on the selectivity and productivity of the oxygenation process. The mixed metal oxide catalysts of the present invention are prepared by an appropriate combination of the metal components, yielding a catalyst with a unique ability to selectively oxidize olefins to alpha-beta unsaturated aldehydes.

SUMMARY OF THE INVENTION

The present invention relates to the selective oxidation of hydrocarbons or olefins in the presence of molecular oxygen to form alpha-beta unsaturated aldehydes. This gas phase reaction is preferably carried out using a mixed metal oxide catalyst at temperatures in the range of 150° C. to 450° C. and at pressures of 1–50 bar. As a result, the method of the present invention achieves relatively high rates of selectivity and productivity.

The catalysts of the present invention are mixed metal oxides of the general formula $$Mo_a Pd_b Bi_c Fe_d X^1_e X^2_f X^3_g O_z,$$

wherein:
- $X^1$ is at least one element selected from the group consisting of Co, Ni, V, Pt, and Rh;
- $X^2$ is at least one element selected from the group consisting of Al, Ga, Ge, Mn, Nb, Zn, Ag, P, Si, and W;
- $X^3$ is at least one element selected from the group consisting of K, Mg, Rb, Ca, Sr, Ba, Na, and In;
- a is 1;
- b is $0<b<0.3$, preferably $0.0000001<b<0.2$;
- c is $0<c<0.9$, preferably $0.0001<c<0.5$;
- d is $0<d<0.9$, preferably $0.0001<d<0.5$;
- e is $0<e<0.9$, preferably $0.0001<e<0.5$;
- f is $0<f<0.9$, preferably $0.0001<f<0.9$;
- g is $0<g<0.3$, preferably $0.0000001<g<0.3$; and
- z is an integer representing the number of oxygen atoms required to satisfy the valency of the remaining components of the formula. The catalysts are preferably produced using the methods disclosed herein.

DETAILED DESCRIPTION OF THE PREFERRED EMBODIMENTS

One aspect of the invention relates to a catalyst for the production of alpha-beta unsaturated aldehydes from olefins and hydrocarbons. According to one embodiment, the catalyst composition has the formula:

$$Mo_a Pd_b Bi_c Fe_d X^1_e X^2_f X^3_g O_z,$$

wherein
- $X^1$ is at least one element selected from the group consisting of Co, Ni, V, Pt, and Rh;
- $X^2$ is at least one element selected from the group consisting of Al, Ga, Ge, Mn, Nb, Zn, Ag, P, Si, and W;
- $X^3$ is at least one element selected from the group consisting of K, Mg, Rb, Ca, Sr, Ba, Na, and In;
- a is 1;
- b is $0 \leq b<0.3$, preferably $0.0000001<b<0.2$;
- c is $0 \leq c<0.9$, preferably $0.0001<c<0.5$;
- d is $0 \leq d<0.9$, preferably $0.0001<d<0.5$;
- e is $0 \leq e<0.9$, preferably $0.0001<e<0.5$;
- f is $0 \leq f<0.9$, preferably $0.0001<f<0.9$;
- g is $0 \leq g<0.3$, preferably $0.0000001<g<0.3$; and
- z is an integer representing the number of oxygen atoms required to satisfy the valency of the remaining components of the formula.

According to a preferred embodiment of the invention, the catalyst composition has the general formula $$Mo_a Pd_b Bi_c Fe_d X^1_e X^2_f X^3_g O_z,$$

wherein:
- $X^1$ is at least one element selected from the group consisting of Co, Ni, V, Pt, and Rh;
- $X^2$ is at least one element selected from the group consisting of Al, Ga, Ge, Mn, Nb, Zn, Ag, P, Si, and W;
- $X^3$ is at least one element selected from the group consisting of K, Mg, Rb, Ca, Sr, Ba, Na, and In;
- a is 1;
- b is $0<b<0.3$, preferably $0.0000001<b<0.2$;
- c is $0<c<0.9$, preferably $0.0001<c<0.5$;
- d is $0<d<0.9$, preferably $0.0001<d<0.5$;
- e is $0<e<0.9$, preferably $0.0001<e<0.5$;
- f is $0<f<0.9$, preferably $0.0001<f<0.9$;
- g is $0<g<0.3$, preferably $0.0000001<g<0.3$; and
- z is an integer representing the number of oxygen atoms required to satisfy the valency of the remaining components of the formula. The catalysts are preferably produced using the methods disclosed herein.

Preferably, the catalyst is prepared from a solution of soluble compounds (salts, complexes, or other compounds) of each of the metals. The solution is preferably an aqueous system having a pH of 1 to 10, and more preferably at a pH of 1 to 7, and the solution is maintained at a temperature of about 30° C. to about 100° C. Water is removed by filtration to complete dryness, at which point the catalyst is dried in an oven at 100° C. to 130° C. for about 4 to about 24 hours. The dried catalyst is calcined by heating to about 250° C. to about 600° C., about 250° C. to about 450° C., in air or oxygen for about one hour to about 16 hours to produce the desired catalyst composition.

The catalyst may be used with or without a support. If desired, suitable supports include alumina, silica, titania, zirconia, zeolites, silicon carbide, molybdenum carbide, molecular sieves, microporous materials, nonporous materials and mixtures thereof. Support material can be pre-treated with acids such as HCl, $HNO_3$, $H_2SO_4$, per acids or heteroploy acids of phosphorous tungstate or silicotunstate, and alkali bases such as KOH or NaOH. When used on a support, the support usually comprises from about 50 to 95% by weight of the catalyst composition, with the remainder being the catalyst composition.

Preferably, molybdenum is introduced into the solution as an ammonium salt, such as ammonium paramolybdate, or as an organic acid salt of molybdenum, such as acetates, oxalates, mandelates, and glycolates. Some other partially water soluble molybdenum compounds which may be used in the present invention include molybdenum oxides, molybdic acid, and molybdenum chlorides.

Preferably, vanadium, bismuth, iron, cobalt, aluminum, gallium, silicon, germanium, antimony, phosphorous, niobium, potassium, magnesium palladium, tungsten, manganese are introduced as salts or acids, oxides, hydrate oxides, acetates, chlorides, nitrates, oxalates, or tartrates.

The method of the present invention is suitable for oxidation of hydrocarbons and olefins to alpha-beta unsaturated aldehydes. Preferably, the feedstock includes lower branched or straight-chained alkanes or alkenes, having $C_2$–$C_6$ carbon atoms. Further, the inventive catalyst can also be applied for the ammoxidation of $C_2$–$C_5$. In a preferred embodiment the starting material is propylene and acrolein is produced by the method.

The reaction mixture used in the method of the present invention is generally a gaseous mixture of 0.1 to 99 mol % olefins, such as propylene, 0.1 to 99 mol % molecular oxygen, either as pure oxygen or in the form of air, 0 to 50 mol % water, in the form of steam, and 0 to 90 mol % nitrogen or another inert gas. The gaseous mixture is generally introduced into the reaction zone at a temperature of about 150° C. to about 500° C., preferably from 250° C. to 450° C. The reaction zone generally has a pressure of from 1 to 50 bar, and preferably 1 to 30 bar. The contact time between the reaction mixture and the catalyst is preferably about 0.01 second to 100 seconds, and more preferably 0.1 second to 10 seconds, and the space hourly velocity is about 50 to about 50,000 $h^{-1}$, preferably about 100 to about 20,000 $h^{-1}$, and more preferably from 500 to 10,000 $h^{-1}$.

According to one preferred embodiment, the method comprises contacting a feed mixture comprising 1–50% by volume of olefins, 0.25 to 50% by volume oxygen or a gas capable of providing oxygen, 0–50% by volume steam and 10–80% by volume inert gas at a temperature of 170 to 450° C. at a pressure of 15–500 psi at a space velocity of 500–20,000 hr-1 with the catalyst. Preferably, the method provides a conversion greater than 90%, more preferably greater than 95%, most preferably greater than 98%, and a selectivity greater than 85%, more preferably greater than 90%, most preferably greater than 95%, of the olefins to the unsaturated aldehydes.

The process is generally carried out in a single stage in a fixed bed or fluidized bed or solid moving bed reactor with all the oxygen and reactants being supplied as a single feed and unreacted starting materials being recycled. However, multiple stage addition of oxygen to the reactor with intermediate hydrocarbon feed can be used. This may improve productivity and avoid a potentially hazardous condition.

The following examples are intended to be illustrative of this invention. They are, of course, not to be taken to in any way limit the scope of this invention. Numerous changes and modifications can be made with respect to the invention without departing from the spirit or scope of the present invention.

EXAMPLES

Example 1

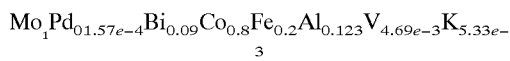

Ammonium metavanadate (Aldrich Chemicals, Assay= 99.0%), 0.11 grams, was added to distilled water and heated to 90° C. with stirring. A yellow colored solution with pH between 4 and 7 was obtained (solution A). Bismuth nitrate, 8.75 g, 16.2 grams of ferric nitrate, and 46.68 grams of cobaltus nitrate were added with water to solution A with continuous stirring. Thereafter, the required amount of palladium, potassium and aluminum salt solutions were slowly added to the mixture. Ammonium paramolybdate tetrahydrate (Aldrich Chemicals A.C.S-12054-85-2), 35.4 grams, was added to the solution. This mixture was then dried. The resulting solid was dried in an oven at 100–120° C. The dried material was cooled to room temperature and calcined in the range of 300 to 600° C. Calcined catalyst was formulated into uniform particles of 40–60 mesh size and loaded in a stainless steel fixed bed tubular autoclave reactor.

The catalyst was tested with a gas feed composition of nitrogen:oxygen:propylene: water in the ratio of 77:7.50:5.50:10 at 342° C., at a pressure of 15 psi, and a total flow of 130 cc/min. The reaction product showed a 99% conversion of propylene with a 98% selectivity for acrolein.

Example 2

Ammonium metavanadate (Aldrich Chemicals, Assay= 99.0%), 0.11 grams, was added to distilled water and heated to 90° C. with stirring. A yellow colored solution with pH between 4 and 7 was obtained (Solution A). Bismuth nitrate, 8.75 g, 16.2 grams of ferric nitrate, and 46.68 grams of cobaltus nitrate were added with water to solution A with continuous stirring, followed by the addition of the required amount of palladium and aluminum salts solution slowly to the mixture. Thereafter, ammonium 35.4 g paramolybdate tetrahydrate (Aldrich Chemicals A.C.S-12054-85-2) was added to the above solution. This mixture was then dried and the resulting solid was dried in an oven at 100–120° C. The dried material was cooled to room temperature and calcined in the range of 300 to 600° C. Calcined catalyst was formulated into uniform particles of 40–60 mesh size and loaded in a stainless steel fixed bed tubular autoclave reactor.

The catalyst was tested with a gas feed composition of nitrogen:oxygen:propylene: water in the ratio of 77:7.50:5.50: 10 at 342° C., at a pressure of 15 psi and a total flow of 130 cc/min. The reaction product showed a 93.2% conversion of propylene with a 87.4% selectivity for acrolein Example 3

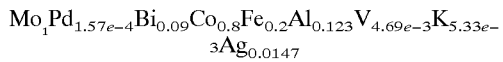

Ammonium metavanadate (Aldrich Chemicals, Assay= 99.0%), 0.11 grams, was added to distilled water and heated to 90° C. with stirring. A yellow colored solution with pH between 4 and 7 was obtained (Solution A). Bismuth nitrate, 8.75 g, 16.2 grams of ferric nitrate, and 46.68 grams of cobaltus nitrate were added with water to solution A with continuous stirring, at which point the required amount of palladium, potassium, silver, and aluminum salt solutions were slowly to the mixture. Thereafter, 35.4 g ammonium paramolybdate tetrahydrate (Aldrich Chemicals A.C.S-12054-85-2) was added to the solution. This mixture was then dried and the resulting solid was dried in an oven at 100–120° C. The dried material was cooled to room temperature and calcined in range of 300 to 600° C. Calcined catalyst was formulated into uniform particles of 40–60 mesh size and loaded in a stainless steel fixed bed tubular autoclave reactor.

The catalyst was tested with a gas feed composition of nitrogen: oxygen: propylene: water in the ratio of 77:7.50:5.50: 10 at 342° C., at a pressure of 15 psi, and a total flow of 130 cc/min. The reaction product showed a 97% conversion of propylene with a 98.6% selectivity for acrolein.

The catalysts disclosed in the present application exhibit modified optimum redox behavior resulting in higher activity and yields towards the oxygenated products. Further, the inventive catalyst showed no deactivation until 8000 hrs on stream and achieved similar or higher yields (>95%) at relatively lower temperatures than mentioned in the prior art.

The above description of the invention is intended to be illustrative and not limiting. Various changes or modifications in the embodiments described may occur to those skilled in the art. These can be made without departing from the spirit or scope of the invention.

What is claimed is:

1. A method for the production of unsaturated aldehydes from olefins, said method comprising contacting said olefins with an oxygen-containing gas in the presence of a catalyst in a reaction zone, said catalyst containing a catalyst composition of the formula:

$$Mo_aPd_bBi_cFe_dX^1_eX^2_fX^3_gO_z,$$

wherein:
 $X^1$ is at least one element selected from the group consisting of Co, Ni, V, Pt, and Rh;
 $X^2$ is at least one element selected from the group consisting of Al, Ga, Ge, Mn, Nb, Zn, Ag, P, Si, and W;
 $X^3$ is at least one element selected from the group consisting of K, Mg, Rb, Ca, Sr, Ba, Na, and In;
 a is 1;
 b is $0<b<0.3$;
 c is $0<c<0.9$;
 d is $0<d<0.9$;
 e is $0<e<0.9$;
 f is $0<f<0.9$;
 g is $0<g<0.3$; and
 z is an integer representing the number of oxygen atoms required to satisfy the valency of Mo, Pd, Bi, Fe, $X^1$, $X^2$, and $X^3$ in the catalyst composition.

2. The method of claim 1, wherein said catalyst is a supported catalyst comprising a support.

3. The method of claim 2, wherein said support is selected from the group consisting of alumina, silica, titania, zirconia, zeolites, silicon carbide, Mo-carbide, molecular sieves, microporous materials, nonporous materials, and mixtures thereof.

4. The method of claim 2, wherein said support is pretreated with an acid or base.

5. The method of claim 2, wherein the supported catalyst comprises from about 5–50% by weight of the catalyst composition, with remainder being the support material.

6. The method of claim 1, wherein the aldehydes are alpha-beta unsaturated.

7. The method of claim 1, wherein the olefins are lower branched or straight-chained, having 2–6 carbon atoms.

8. The method of claim 1, wherein said olefin is propylene and said method produces acrolein.

9. The method of claim 4, wherein said acid is selected from HCl, $HNO_3$, $H_2SO_4$, heteroploy acids of phosphorous tungstate or silicotungstate or mixtures thereof.

10. The method of claim 2, wherein said support is pretreated with a base selected from the group consisting of KOH, NaOH or mixtures thereof.

11. The method of claim 1, wherein said method comprises contacting a feed mixture comprising 1–50% by volume of olefins, 0.25 to 50% by volume oxygen or a gas capable of providing oxygen, 0–50% by volume steam and 10–80% by volume inert gas at a temperature of 170 to 450° C. at a pressure of 15–500 psi at a space velocity of 500–20,000 hr−1 with the catalyst, and wherein said method provides a conversion greater than 98% and selectivity greater than 95% of said olefins to said unsaturated aldehydes.

12. The method of claim 11, wherein said olefins comprise propylene.

13. The method of claim 11, wherein said catalyst is in the form of a fixed or fluidized bed or solid moving bed reactor.

14. The method of claim 1, wherein said oxygen-containing gas comprises molecular oxygen.

15. The method of claim 11, further comprising the multi-step introduction of oxygen into the reaction zone to increase the yield, selectivity or both yield and selectivity of the corresponding unsaturated aldehydes.

* * * * *

UNITED STATES PATENT AND TRADEMARK OFFICE
CERTIFICATE OF CORRECTION

PATENT NO.      : 6,337,424 B1
DATED           : January 8, 2002
INVENTOR(S)     : Karim et al.

It is certified that error appears in the above-identified patent and that said Letters Patent is hereby corrected as shown below:

<u>Title pasge, Item [54] and Column 1, lines 1-4,</u>
Title, should read -- CATALYSTS FOR OXIDATION OF LOWER OLEFINS TO UNSATURATED ALDEHYDES, METHODS OF MAKING AND USING THE SAME --

Signed and Sealed this

Eighteenth Day of May, 2004

JON W. DUDAS
*Acting Director of the United States Patent and Trademark Office*